United States Patent [19]

Modrovich et al.

[11] Patent Number: 5,221,615
[45] Date of Patent: Jun. 22, 1993

[54] LIQUID STABLE TRIGLYCERIDE REAGENT SYSTEM

[75] Inventors: Ivan E. Modrovich, 1043 Mesa Dr., Camarillo, Calif. 93010; Ralph E. Bolstad, Anaheim; Paul F. Wegfahrt, Jr., Camarillo, both of Calif.

[73] Assignee: Ivan E. Modrovich, Camarillo, Calif.

[21] Appl. No.: 794,177

[22] Filed: Nov. 14, 1985

[51] Int. Cl.$^5$ .................. C12N 9/96; C12Q 1/44; C12Q 1/48
[52] U.S. Cl. .................. 435/15; 435/19; 435/25; 435/28; 435/188; 435/810; 436/13
[58] Field of Search .......... 435/15, 18, 28, 810, 435/188, 19, 25; 436/13; 252/174.12

[56] References Cited

U.S. PATENT DOCUMENTS

| | | | |
|---|---|---|---|
| 3,963,578 | 6/1976 | Aitken et al. | 435/188 X |
| 4,169,817 | 10/1979 | Weber | 252/174.12 X |
| 4,241,178 | 12/1980 | Esders et al. | 435/15 |
| 4,250,254 | 2/1981 | Modrovich | 435/188 X |
| 4,368,261 | 1/1983 | Klose et al. | 435/15 |
| 4,378,429 | 5/1983 | Modrovich | 435/188 |
| 4,608,335 | 8/1986 | Fossati | 435/15 X |

OTHER PUBLICATIONS

Good et al., Biochemistry, 5(2): 467–476 (1966).

*Primary Examiner*—Mary E. Ceperley
*Assistant Examiner*—Toni R. Scheiner
*Attorney, Agent, or Firm*—Christie, Parker & Hale

[57] ABSTRACT

A stable triglyceride assay solution for use with a chromogen system is comprised of a solution buffered with a Zwitterionic buffering agent and/or TRIS and stabilized with sortibol, gelatin, and ammonium sulfate. Solution pH is in the range of from 6.8 to 8.0. The functional enzymes are lipase, glyercol kinase, and glycerol phosphate oxidase. The preferred chromogen system is based on the inclusion of 4-aminoantipyrine for use in combination with oxidase to yield a detectable chromogen compound.

12 Claims, No Drawings

LIQUID STABLE TRIGLYCERIDE REAGENT SYSTEM

BACKGROUND OF THE INVENTION

It has been known to determine triglycerides in sera and other substrates by processes as described in U.S. Pat. No. 4,241,178 to Esders and Goodhue, incorporated herein by reference.

The reactions involved are:

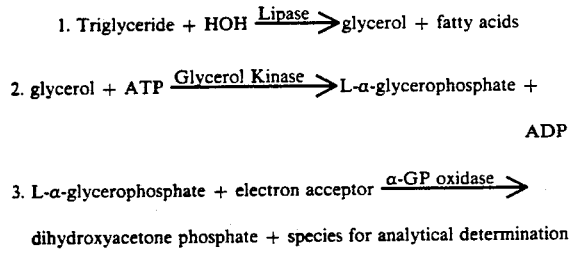

When oxygen is the electron acceptor, $H_2O_2$ is formed as the species for analytical determination in (3), and $H_2O_2$ determination is preferably accomplished according to the following reaction:

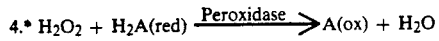

*$H_2A$ (red) = dye precursor which is the reduced form of the dye
$A(ox)$ = dye formed by oxidation of $H_2A$ The amount of triglycerides present may be determined in modern technique by measuring the amount of hydrogen peroxide through the use of a suitable chromogen system.

Our preferred chromogen system is based on the use of peroxidase, typically from a horseradish source, a phenol such as p-chlorophenol (pCP), and 4-aminoantipyrene (4AAP), involving the reaction:

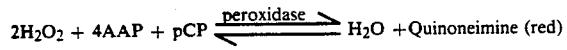

The intensity of the red quinoneimine formed is measured at 500 nm.

As most assay systems are based on enzymes, the proposed system is prone to rapid degradation. As a consequence, the art early-on lyophilized (freeze-dried) the system for reconstitution at the time of use. Lyophilization is expensive and decreases the accuracy of assay procedures. Lifetime of reconstituted solution is short.

SUMMARY OF THE INVENTION

It has now feen found that one can formulate a two-component liquid stabilized system suited to the determination of triglyceride content in sera.

The first component of the system is a stable triglyceride enzyme system which comprises an aqueous solution of at least one Zwitterionic buffer and/or tris(hydroxymethyl)amino ethane (TRIS), lipase, glyercol kinase, and glyercol phosphate oxidase, stabilized by a system comprising gelatin, a nonreactive hydroxy organic compound unrelated to glycerine, preferably sorbitol, and ammonium sulfate.

The buffer system is provided in a concentration sufficient to maintain pH in the range of from about 6.0 to about 8.0, preferably about 7.0. The presently preferred stabilizing system provides gelatin in a concentration of from about 0.05 to about 0.7, preferably 0.5, percent weight-by-volume; sorbitol in a concentration of from about 5 to about 40, preferably about 25, percent weight-by-volume; and ammonium sulfate in a concentration of from about 0.05 to about 15, preferably about 1, molar, based on the total amount of the triglyceride enzyme system.

The preferred buffers are 3-(4-morpholino)propanesulfonic acid (MOPS) in combination with TRIS.

The preferred chromogen system comprises magnesium chloride as a cofactor, and a phenol derivative such as p-chlorophenol, in admixture with ATP, 4-aminoantipyrene, magnesium chloride, and peroxidase as the enzyme. Gelatin and at least one Zwitterionic buffering agent such as MOPS and/or TRIS, are employed to give good shelf-life, when combined with the triglyceride assay system to give a total system. Additional components include ethylene triamine tetraacetic acid (EDTA-Na), and polyethylene glycol p-isooctylphenyl ether (Triton X-100). For commercial practicality, the two components are combined in proportion to enable completion of the reaction within ten minutes at room temperature (25° C.), with color stability lasting at least an additional thirty minutes.

DETAILED DESCRIPTION

According to the present invention, there is provided a stable liquid assay system for the determination of triglycerides in sera, the components of which display a protracted shelf-life, i.e., a shelf-life in excess of about eighteen months or more, at 4° C. (refrigeration conditions). Long shelf-life is primarily the result of the selection of a buffer and a stabilizer system, as described herein.

A stable triglyceride assay system of the instant invention comprises an aqueous triglyceride enzyme solution to form products for a chromogen assay, and a chromogen solution for combination therewith.

The stable aqueous triglyceride enzyme solution typically comprises at least one organic, Zwitterionic buffering agent having a pKa between 6.15 and 8.15, alone and/or with another organic buffer such as TRIS, the total buffering agent normally being present in a concentration of from about 10 to about 200 mM and sufficient to maintain pH at between about 6.0 and about 8.0, preferably at about 7.0; lipase, preferably from microbial sources; glycerol kinase, preferably from *Bacillus stearothermophilus* and *E. Coli*; glycerol phosphate oxidase; and a stabilizer system based on a nonreactive hydroxy organic compound which bears no structural identity to glycerine, preferably sorbitol, gelatin and ammonium sulfide.

By "a nonreactive hydroxy organic compound which bears no structural identity to glycerine", there is meant a compound which does not enter into reaction with the product of the enzyme-catalyzed reactions to deprive the system of a product or to resemble a product, so as to introduce error into the amount of triglyceride that is determined to have entered into the assay reactions.

The presently preferred stabilizer system for the invention is summarized in Table I.

TABLE I

|  | Preferred Qty. | Qty. Range | Comments |
|---|---|---|---|
| Buffer | 25 mM | 10–200 |  |
| pH | 7.0 | 6.0–8.0 |  |
| Gelatin | 0.5% w/v | 0.05–0.7 | Gels above 0.7% |
| Sorbitol | 25% w/v | 5–40 | Viscous at high concentrations. |
| Ammonium Sulfate | 1.0 Molar | 0.5–1.5 | Inhibits reaction > 1.5. |

The presently preferred triglyceride enzyme solution is shown in Table II, in total liter quantity.

TABLE II

| Compound | Unit | Qty. | Total |
|---|---|---|---|
| Distilled H$_2$O | liter | 0.7000 | 0.7000 |
| MOPS | gram | 5.2300 | 5.2300 |
| TRIS | gram | 1.5100 | 1.5100 |
| K$_4$Fe(CN)$_6$.3H$_2$O | gram | 0.8450 | 0.8450 |
| Lipase - Genzyme | KIU | 2000.0000 | 2000.0000 |
| Lipase - Toyobo | KIU | 33.0000 | 33.0000 |
| Glycerol Kinase | KIU | 20.0000 | 20.0000 |
| Glycerol Phosph. Oxidase | KIU | 300.0000 | 300.0000 |
| Ammonium Sulfate* | gram | 132.1400 | 132.1400 |
| Gelatin | gram | 5.8000 | 0.3000 |

*1.0 Molar

Other buffering agents may be employed. Included are organic Zwitterionic buffers having a pKa of from about 6.15 to about 8.15. Among those which may be mentioned are: 2-(4-morpholino)ethanesulfonic acid (MES), N-[2-acetamido)amino]diacetic acid (ADA), 2-[bis(2-hydroxyethyl)amino]-2-hydroxymethyl)-1,3-propanediol (BIS-TRIS PROPANE), 1,4-piperazine diethanesulfonic acid (PIPES), N-(2-acetamido)-2-aminoethanesulfonic acid (ACES), N-[2-hydroxy-1,1-bis(hydroxymethyl)ethyl]taurine (TES), N,N-bis(2-hydroxyethyl)-1-1-piperazineethanesulfonic acid (HEPES), N,N-bis(2-hydroxyethyl)glycine (BICNE), 3-cyclohexylamino)propanesulfonic acid (CAPS), and the like.

The glyercol kinase derived from *Candida mycoderma* has generally proven to be unsatisfactory.

While a wide variety of chromogen systems enabling the detection of triglyceride may be employed, Table III lists, in the amounts required to provide one liter of solution, the presently preferred chromogen solutions.

TABLE III

| Compound | Unit | Qty. |
|---|---|---|
| Gelatin | gram | 1.0000 |
| MOPS | gram | 10.4600 |
| TRIS | gram | 3.0300 |
| ATP | gram | 0.4240 |
| Magnesium Chloride | gram | 1.0000 |
| EDTA-Na$_2$ | gram | 0.7450 |
| 4-Aminoantipyrine | gram | 0.1018 |
| p-Chlorophenol | gram | 0.5000 |
| Triton X-100 | ml | 0.0500 |
| Peroxidase | KIU | 20.0000 |
| Distilled H$_2$O | liter | Balance |

Using the preferred compositions of the invention, chromogen solutions and enzyme solutions are combined in the ratio of 100 parts chromogen solution to one part enzyme solution. The stability of the net working reagent is about two weeks at a temperature of from 2° to 8° C., and is comparable to the freeze-dried reagents. The stability of the separate components is conservatively estimated to be eighteen months at a temperature of from 2° to 8° C., based on accelerated stability testing at 41° C. The components show no significant deterioration of performance in the triglycerides assay after 3-5 days' incubation at this temperature. In addition, sample kits which have been stored for six months at a temperature of from 2° to 8° C., have shown no deterioration in performance.

What is claimed is:

1. A two component liquid stabilized system for use in the determination of triglyceride content of sera, which system consists of a triglyceride enzyme system capable of generating hydrogen peroxide form triglycerides and a chromogen system for responding to generated hydrogen peroxide in which the triglyceride enzyme system comprises an aqueous solution of at least one buffering agent selected from the group consisting of Zwitterionic buffering agents having a pKa of between about 6.15 and about 8.15, tris (hydroxymethyl)-amino ethane, and mixtures thereof, said buffering agent present in a concentration sufficient to maintain pH in the range of from about 6.0 to about 8.0, and, as enzymes, lipase, glycerol kinase and glyercol phosphate oxidase, said triglyceride enzyme system containing, in addition to said buffering agent and enzymes a non-buffering stabilizer for said triglyceride enzyme system which comprises a stabilizing amount of a nonreactive hydroxy organic compound which bears no structural identity to glycerine, gelatin in an amount of about 5 to 40 weight-by-volume of solution, and ammonium sulfate in an amount of from about 0.5 to 1.5 molar, said two component liquid stabilized system having, in an uncombined state, a shelf life of at least about 18 months at 2° to 8° C.

2. A system as claimed in claim 1 in which the chromogen system comprises a phenol derivative, ATP, magnesium chloride, peroxidase, and 4-aminoantipyrine in a concentration sufficient to provide a colorimetric quantitative determination of hydrogen peroxide within about 10 minutes.

3. A composition as claimed in claim 2 in which the phenol derivative is p-chlorophenol.

4. A two component liquid stabilized system for the determination of a triglyceride content of sera, which system consists of triglyceride enzyme system and a chromogen system and in which the triglyceride enzyme system comprises an aqueous solution containing for each liter of distilled water, at least one buffer selected from the group consisting of a Zwitterionic buffering agent having a pKa between 6.15 and 8.15 and tris(hydroxymethyl)amino ethane and mixtures thereof, said buffer present in a concentration of from about 10 to about 200 mM per liter, and sufficient to maintain pH at about 6.0 to about 8.0, potassium ferrocyanide in an amount of about 20 KIU, glyercol, phosphate oxidase in a concentration of 300 KIU, gelatin in a concentration of from about 0.05 to about 0.7 percent weight-by-volume of solution, and a stabilizer for the triglyceride enzyme system which comprises sorbitol in a concentration of from about 5 to about 40 percent weight-by-volume of solution, and ammonium sulfate in a concentration of from about 0.5 to about 1.5 molar and in which the chromogen system comprises ATP, magnesium chloride, peroxidase, and 4-aminoantipyrine in a concentration sufficient to provide a colorimetric quantitative determination of hydrogen peroxide within about 10 minutes, said liquid stabilized system having in an uncombined state a shelf life of at least about 18 months at 2° to 8° C.

5. A system as claimed in claim 4 in which the stabilizer for the triglyceride enzyme system comprises gelatin in an amount of about 0.5 percent weight-by-volume of solution, sorbitol in a concentration of about 25 percent weight-by-volume of solution, and ammonium sulfate in a concentration of about 1.0 molar.

6. A system as claimed in claim 4 in which the buffer is present in a concentration of about 25 mM, and pH is about 7.

7. A system as claimed in claim 6 in which gelatin is present in a concentration of about 0.5 percent weight-by-volume of solution, and ammonium sulfate is present in a concentration of about 1 molar.

8. A system as claimed in claim 7 in which the buffer is a mixture of 3-(4-morpholino)propanesulfonic acid and tris(hydroxymethyl)amino ethane.

9. A system as claimed in claim 8 in which glyercol kinase is from *Bacillus stearothermophilus* or *E. coli*.

10. A system as claimed in claim 4 in which the triglyceride enzyme system in combination with a chromogen system for triglyceride detection comprising for each liter thereof, at least one buffering agent selected from the group consisting of a Zwitterionic buffer having a pKa between 6.15 and 8.15 tris(hydroxymethyl)amino ethane and mixtures thereof present in a concentration to provide a pH of from about 6 to about 8, ATP present in an amount of about 0.424 gram, magnesium chloride present in an amount of about 1 gram, the sodium salt of ethylene diamine tetraacetic acid present in an amount of about 0.745 gram, 4-aminoantipyrine present in an amount of about 0.1118 gram, p-chlorophenol present in an amount of about 0.05 gram, peroxidase present in an amount of about 10 KIU, polyethylene glycol-p-isooctylphenyl ether present in an amount of about 0.05 gram, the balance being distilled water.

11. A system as claimed in claim 7 in combination with a chromogen system comprising for each liter thereof, at least one buffering agent selected from the group consisting of a Zwitterionic buffer having a pKa between 6.15 and 8.15 tris(hydroxymethyl)amino ethane and mixtures thereof present in a concentration to provide a pH of from about 6 to about 8, ATP present in an amount of about 0.424 gram, magnesium chloride present in an amount of about 1 gram, the sodium salt of ethylene diamine tetraacetic acid present in an amount of about 0.745 gram, 4-aminoantipyrine present in an amount of about 0.1118 gram, p-chlorophenol present in an amount of about 0.05 gram, peroxidase present in an amount of about 10 KIU, polyethylene glycol-p-isooctylphenyl ether present in an amount of 0.05 gram, the balance being distilled water.

12. A system as claimed in claim 8 in combination with a chromogen system comprising for each liter thereof, at least one buffering agent selected from the group consisting of a Zwitterionic buffer having a pKa between 6.15 and 8.15, tris(hydroxymethyl)amino ethane and mixtures thereof present in a concentration to provide a pH of from about 6 to about 8, ATP present in an amount of about 0.424 gram, magnesium chloride present in an amount of about 1 gram, the sodium salt of ethylene diamine tetraacetic acid present in an amount of about 0.745 gram, 4-aminoantipyrine present in an amount of about 0.1118 gram, p-chlorophenol present in an amount of about 0.05 gram, peroxidase present in an amount of about 10 KIU, polyethylene glycol-p-isooctylphenyl ether present in an amount of about 0.05 gram, the balance being distilled water.

* * * * *

UNITED STATES PATENT AND TRADEMARK OFFICE
CERTIFICATE OF CORRECTION

PATENT NO. : 5,221,615
DATED : June 22, 1993
INVENTOR(S) : Ivan E. Modrovich, et. al.

It is certified that error appears in the above-indentified patent and that said Letters Patent is hereby corrected as shown below:

Column 1, line 53, change "solution" to -- solutions --.

Column 1, line 56, change "feen" to -- been --.

Column 4, line 54, change "glyercol" to -- glycerol --.

Signed and Sealed this

Fifteenth Day of March, 1994

Attest:

BRUCE LEHMAN

Attesting Officer   Commissioner of Patents and Trademarks